(12) United States Patent
Zuluaga

(10) Patent No.: US 9,198,579 B2
(45) Date of Patent: Dec. 1, 2015

(54) METHOD AND DEVICE FOR THE OPTICAL SPECTROSCOPIC IDENTIFICATION OF CERVICAL CANCER

(75) Inventor: Andres Felipe Zuluaga, Houston, TX (US)

(73) Assignee: Remicalm, LLC, Houston, TX (US)

( * ) Notice: Subject to any disclaimer, the term of this patent is extended or adjusted under 35 U.S.C. 154(b) by 206 days.

(21) Appl. No.: 13/469,269

(22) Filed: May 11, 2012

(65) Prior Publication Data

US 2012/0226167 A1    Sep. 6, 2012

Related U.S. Application Data

(63) Continuation of application No. 12/287,801, filed on Oct. 14, 2008, now abandoned, which is a continuation-in-part of application No. 12/229,541, filed on Aug. 25, 2008, now abandoned.

(60) Provisional application No. 60/999,095, filed on Oct. 16, 2007.

(51) Int. Cl.
| | |
|---|---|
| A61B 6/00 | (2006.01) |
| A61B 5/00 | (2006.01) |
| A61B 1/00 | (2006.01) |
| A61B 1/04 | (2006.01) |
| A61B 1/303 | (2006.01) |
| A61B 1/06 | (2006.01) |

(52) U.S. Cl.
CPC ........... *A61B 5/0071* (2013.01); *A61B 1/00039* (2013.01); *A61B 1/00186* (2013.01); *A61B 1/042* (2013.01); *A61B 1/043* (2013.01); *A61B 1/0646* (2013.01); *A61B 1/303* (2013.01); *A61B 5/0075* (2013.01); *A61B 5/0084* (2013.01); *A61B 2560/0437* (2013.01)

(58) Field of Classification Search
USPC .......................................... 600/473, 476–478
See application file for complete search history.

(56) References Cited

U.S. PATENT DOCUMENTS

| | | |
|---|---|---|
| 5,421,339 A | 6/1995 | Ramanujam et al. |
| 5,459,570 A | 10/1995 | Swanson et al. |
| 5,507,287 A | 4/1996 | Palcic et al. |
| 5,591,981 A | 1/1997 | Heffelfinger et al. |
| 5,612,540 A | 3/1997 | Richards-Kortum et al. |
| 5,623,932 A | 4/1997 | Ramanujam et al. |
| 5,697,373 A | 12/1997 | Richards-Kortum et al. |
| 5,699,795 A | 12/1997 | Richards-Kortum et al. |
| 5,749,830 A | 5/1998 | Kaneko et al. |

(Continued)

OTHER PUBLICATIONS

Benavides, et al; Multispectral digital colposcopy for in vivo detection of cervical cancer; Optics Express, vol. 11, No. 10; pp. 1223-1236; May 19, 2003; US.

(Continued)

*Primary Examiner* — Unsu Jung
*Assistant Examiner* — Shahdeep Mohammed
(74) *Attorney, Agent, or Firm* — Elizabeth R. Hall

(57) ABSTRACT

A medical examination device used for the detection of precancerous and cancerous tissue has an illumination source, a visualization unit, a contacting optical probe, a detector and a process unit. One embodiment of the apparatus includes both a non-contacting macroscopic viewing device (the visualization unit) for visualizing an interior surface of the cervix, as well as a fiber optic wand (contacting optical probe) for spectrally analyzing a microscopic view of the tissue.

21 Claims, 14 Drawing Sheets

(56) References Cited

U.S. PATENT DOCUMENTS

| | | |
|---|---|---|
| 5,991,653 A | 11/1999 | Richards-Kortum et al. |
| 6,258,576 B1 | 7/2001 | Richards-Kortum et al. |
| 6,405,070 B1 | 6/2002 | Banerjee |
| 6,571,118 B1 | 5/2003 | Utzlinger et al. |
| 6,593,101 B2 | 7/2003 | Richards-Kortum et al. |
| 6,697,652 B2 | 2/2004 | Georgakoudi et al. |
| 6,697,666 B1 | 2/2004 | Richards-Kortum et al. |
| 6,766,184 B2 | 7/2004 | Utzinger et al. |
| 6,870,616 B2 | 3/2005 | Jung et al. |
| 7,172,553 B2 | 2/2007 | Ueno et al. |
| 7,236,815 B2 | 6/2007 | Richards-Kortum et al. |
| 7,365,844 B2 | 4/2008 | Richards-Kortum et al. |
| 8,386,015 B2 * | 2/2013 | Kamen ............ A61B 6/037 382/128 |
| 2002/0007111 A1 | 1/2002 | Deckert et al. |
| 2002/0007122 A1 | 1/2002 | Kaufman et al. |
| 2002/0171831 A1 | 11/2002 | Backman et al. |
| 2003/0078477 A1 | 4/2003 | Kang et al. |
| 2003/0207250 A1 | 11/2003 | Kaufman et al. |
| 2004/0064053 A1 | 4/2004 | Chang et al. |
| 2004/0186383 A1 | 9/2004 | Rava et al. |
| 2004/0220451 A1 | 11/2004 | Gravenstein et al. |
| 2005/0054937 A1 * | 3/2005 | Takaoka et al. ............ 600/476 |
| 2005/0080343 A1 | 4/2005 | Richards-Kortum et al. |
| 2005/0128488 A1 | 6/2005 | Yelin et al. |
| 2006/0030786 A1 * | 2/2006 | Lu ............................ 600/572 |
| 2006/0171845 A1 | 8/2006 | Martin et al. |
| 2007/0038120 A1 * | 2/2007 | Richards-Kortum et al. 600/476 |
| 2007/0161876 A1 | 7/2007 | Bambot et al. |
| 2007/0213590 A1 | 9/2007 | Squicciarini |
| 2008/0161699 A1 | 7/2008 | Zeng et al. |

OTHER PUBLICATIONS

Medispectra, Inc.; Summary of Safety and Effectiveness Data; LUMA Cervical Imaging System, SSED-P040028; at least as early as Mar. 16, 2006; Lexington, MA; US.

Scott, et al.; Fluorescence Photodiagnostics and Photobleaching Studies of Cancerous Lesions using Ratio Imaging and Spectroscopic Techniques: Lasers Med. Sci. 2000; 16:63-72: no month, 2000; Springer-Vertag London Limited; UK.

USPTO; First Office Action on the Merits for U.S. Appl. No. 12/287,801; Jul. 11, 2011; US.

USPTO; First Office Action for U.S. Appl. No. 12/287,801; Jan. 18, 2012; US.

* cited by examiner

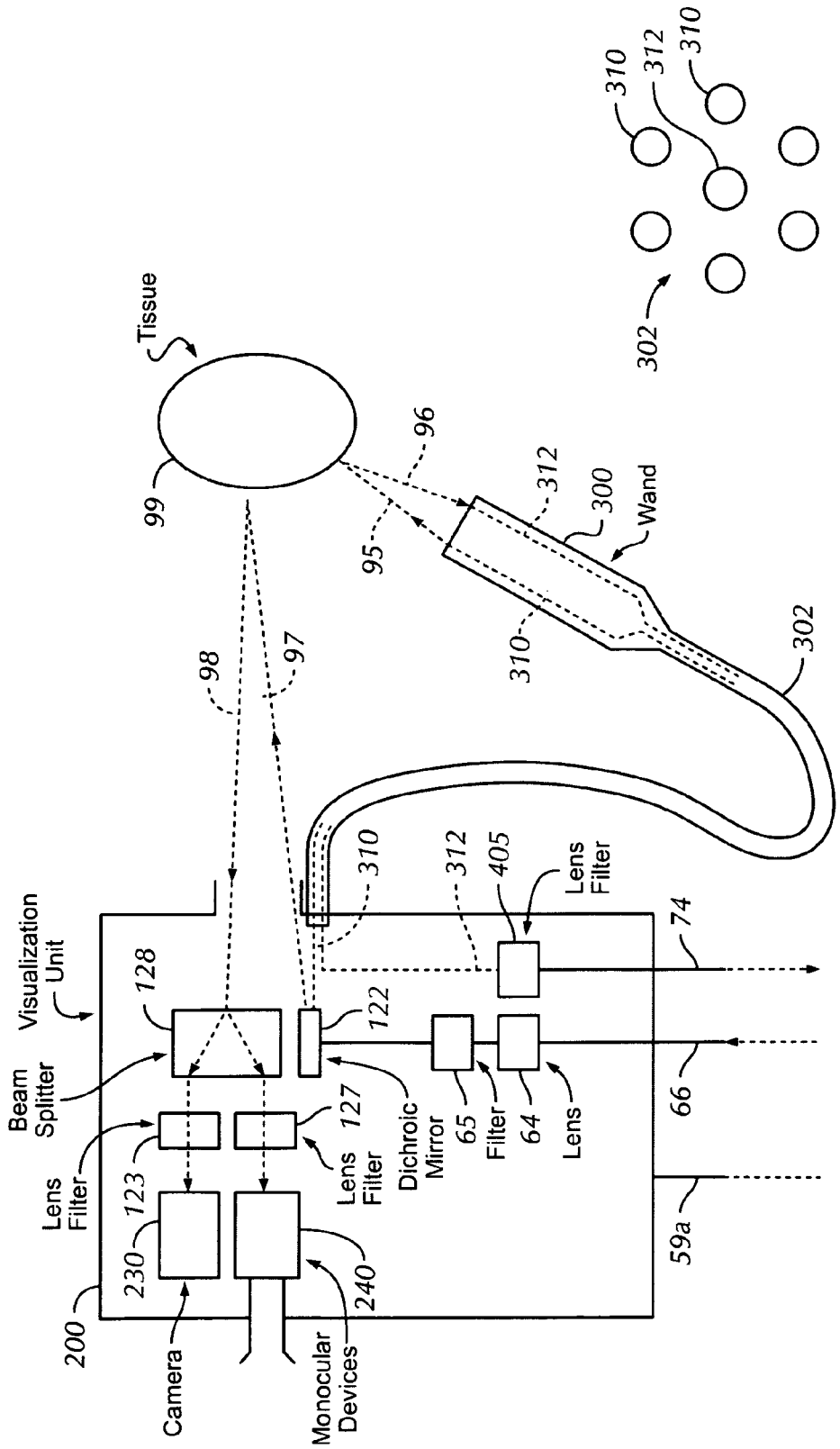

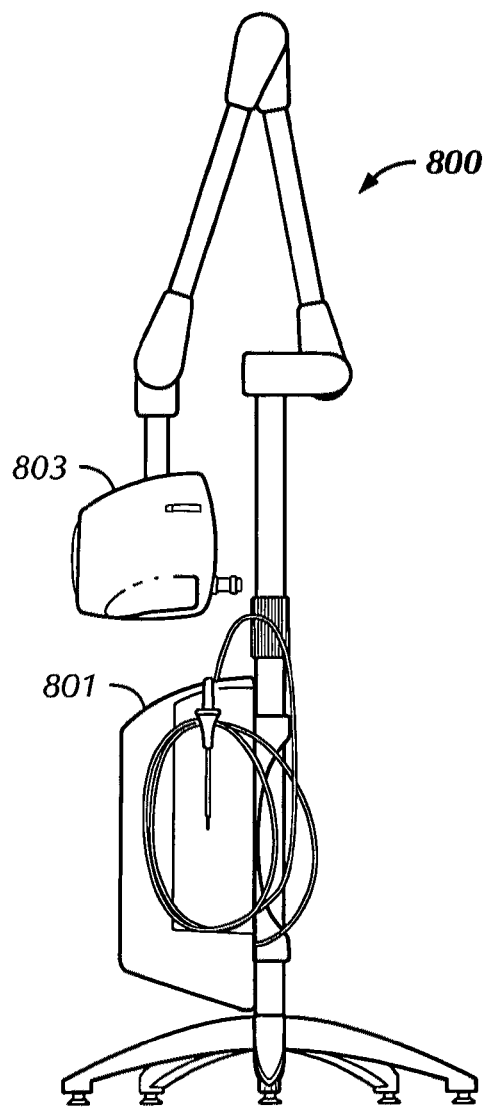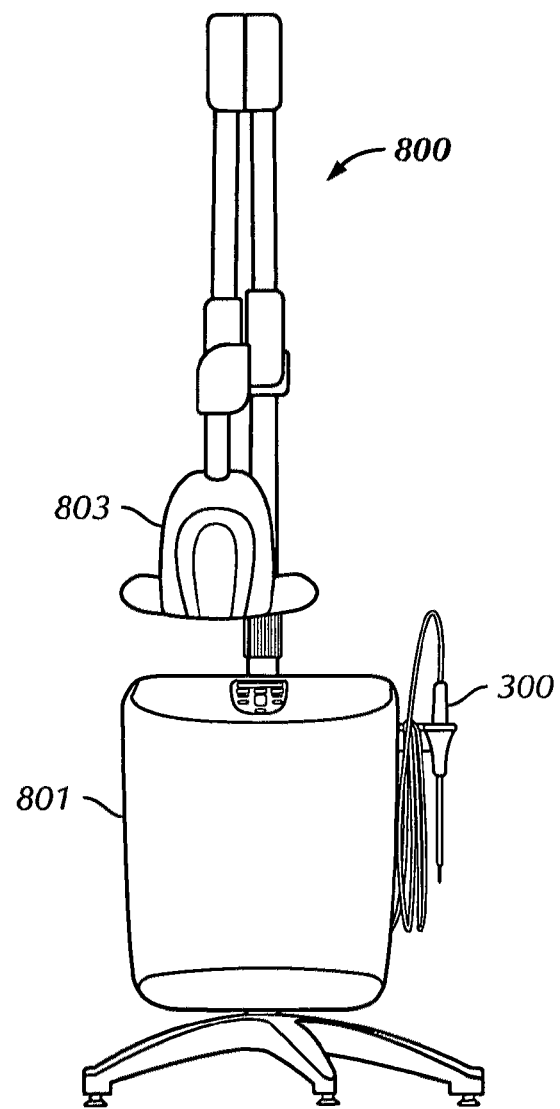
*FIG. 12*
*FIG. 13*

Image Name

1. Reflectance 0 ("Ref White")
2. Reflectance 1 ("Ref Blue")
3. Reflectance 2 ("Ref Violet")
4. Fluorescence 1("Fl UV")
5. Fluorescence 2("Fl Violet")
6. Fluorescence 3("Fl Blue")

METHOD AND DEVICE FOR THE OPTICAL SPECTROSCOPIC IDENTIFICATION OF CERVICAL CANCER

CROSS-REFERENCE TO RELATED APPLICATION

The present application is a continuation of U.S. patent application Ser. No. 12/287,801 filed Oct. 14, 2008 and entitled "Method and Device for the Optical Spectroscopic Identification of Cervical Cancer, which is a continuation-in-part application of U.S. patent application Ser. No. 12/229,541 filed Aug. 25, 2008 and entitled "Optical Spectroscopic Device for the Identification of Cervical Cancer" and, pursuant to 35 U.S.C. 111(b), claims the benefit of the earlier filing date of provisional application Ser. No. 60/999,095 filed Oct. 16, 2007, and entitled "Apparatus for Optical Spectroscopic Identification of Cancer in Clinical Use."

BACKGROUND OF THE INVENTION

1. Field of the Invention

The invention relates to a medical device for use in a clinical environment that utilizes optical spectroscopic means for the identification of cervical pre-cancerous and cancerous conditions. More particularly, the present invention relates to a medical examination apparatus having an illumination source, an optical probe, a visualization unit, a detector, and a processing unit for identifying pre-cancerous and cancerous conditions.

2. Description of the Related Art

Cervical cancer is the second most common malignancy in women worldwide. The mortality associated with cervical cancer can be reduced if this disease is detected at the early stages of development or at the pre-cancerous state. A pap smear is used to screen the general female population for cervical cancer with more than 70 million performed each year in the United States. In spite of its broad acceptance as a screening test for cervical cancer, pap smears probably fail to detect 50-80% Of low grade cancerous lesions and about 15-30% of high grade lesions.

While the pap smear is designed for initial screening, colposcopy and related procedures are typically used to confirm pap smear abnormalities and to grade cancerous and potential cancerous lesions. Although it is generally recognized that colposcopy is highly effective in evaluating patients with abnormal pap smears, colposcopy has its own limitations. Conventional colposcopy is a subjective assessment based on the visual observation of the clinician and the quality of the results depends greatly on the expertise of the practitioner.

Commercially available colposcopes are large free-standing instruments and are generally maintained in a single location (i.e., one examination room). Furthermore, colposcopes are expensive and are typically shared by multiple doctors. Accordingly, when a colposcopic examination is required, the patient has to be brought to the colposcope. Based on the limited availability of the colposcope, a special appointment time separate from the initial appointment is usually required resulting in additional time and cost to a patient as well as delayed examinations.

Accordingly, a portable apparatus, which allows for a close-up visual medical examination would be advantageous for providing an examination without relocation of the patient or providing a separate appointment time. Such an apparatus should be readily useable and economical, thereby making diagnosis and treatment more readily available and cost efficient.

SUMMARY OF THE INVENTION

One embodiment of the invention provides a medical examination device used for the detection of pre-cancerous and cancerous tissue having an illumination source, a visualization unit, a contacting optical probe, a detector and a process unit. A preferred embodiment of the apparatus includes both a non-contacting macroscopic viewing device (the visualization unit) for visualizing the cervix, as well as a fiber optic wand (contacting optical probe) for spectrally analyzing a microscopic view of the tissue.

Another embodiment of the invention is a medical examination device comprising: A medical examination device comprising: an illumination source, wherein the illumination source includes a lamp and a plurality of selectably engageable filters for generating a beam of light of a selected wavelength; a light directing device for selectably directing the beam of light from the lamp in a first beam direction or in a second beam direction; a visualization unit that receives the beam of light whenever the beam of light is directed in the first beam direction and radiates a tissue with the received beam of light, the visualization unit visualizes and captures a macroscopic view of the tissue from a first emitted light beam emanating from the tissue illuminated with the received beam of light; a fiber optic probe having a shaft, a handle, and a fiber optic bundle having a plurality of excitation fiber optic strands and a collection fiber optic strand, wherein whenever the beam of light is directed in the second beam direction the excitation fiber optic strands receive and transmit the beam of light to a selected microscopic tissue area at a site of contact with a distal end of the fiber optic probe, and wherein the collection fiber optic strand collects a second emitted light beam emanating from the tissue area illuminated with the beam of light transmitted by the excitation fiber optic strands; a detector for detecting a plurality of emission wavelengths from the second emitted light beam; and a processor for calculating from the emission wavelengths a probability that the tissue is diseased.

Yet another embodiment of the present invention is a medical examination device comprising: an illumination source, wherein the illumination source includes a lamp and a plurality of selectably engageable filters for generating a beam of light of a selected wavelength; a light directing device for selectably directing the beam of light from the lamp in a first beam direction or in a second beam direction; a visualization unit that receives the beam of light whenever the beam of light is directed in the first beam direction and radiates a tissue with the received beam of light, the visualization unit captures an image of a macroscopic view of the tissue from a first emitted light beam emanating from the tissue illuminated with the received beam of light; a fiber optic probe having a shaft, a handle, and a fiber optic bundle having a plurality of excitation fiber optic strands and a collection fiber optic strand, wherein whenever the beam of light is directed in the second beam direction the excitation fiber optic strands receive and transmit the beam of light to a selected microscopic tissue area at a site of contact with a distal end of the fiber optic probe, and wherein the collection fiber optic strand collects a second emitted light beam emanating from the tissue area illuminated with the beam of light transmitted by the excitation fiber optic strands; a detector for detecting a plurality of emission wavelengths from the second emitted light beam; a user interface unit; and a processor in bi-directional communication with the illumination source, the light directing device, the visualization unit, the fiber optic probe, the detector and the user interface unit.

Still yet another embodiment of the present invention is a method of detecting cervical cancer comprising the steps of: filtering a beam of light from an illumination source with a selection of filters to produce a plurality of desired wavelengths; sequentially transmitting a first set of wavelengths produced from the beam of light to a visualization unit; illuminating a portion of a cervix with the first set of wavelengths transmitted to the visualization unit; capturing an image of a macroscopic view of the cervix illuminated with each of the first set of wavelengths; selecting a microscopic tissue site within the macroscopic view for further investigation; watching the placement of a distal end of a fiber optic probe in contact with the selected microscopic tissue site; activating a light directing device to direct a second set of wavelengths to a plurality of excitation fibers in the fiber optic probe; sequentially transmitting the second set of wavelengths though the excitation fibers to illuminate the selected tissue site; collecting an emitted light beam emanating from the illuminated tissue site through a reception fiber optic strand; conducting a spectral analysis of the collected light using a spectrometer; and calculating a probability that the selected tissue site is cancerous.

The foregoing has outlined rather broadly several embodiments of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed might be readily utilized as a basis for modifying or redesigning the structures for carrying out the same purposes as the invention. It should be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIG. 3 is a schematic view showing the interrelationship of the components of one embodiment of the visualization unit.

FIG. 4 is a schematic view showing the interrelationship of the excitation and collection fiber optic strands in one embodiment of the fiber optic bundle that traverses the optical probe.

FIG. 12 is a side profile view of the device of FIG. 11 in its stowed position.

FIG. 13 is a rear view of the stowed device of FIG. 11.

DESCRIPTION OF THE PREFERRED EMBODIMENTS

The present invention relates to an apparatus and method for obtaining diagnostic evaluations of potential precancerous tissues and cancerous tumors on externally exposed body surfaces. Specifically, the apparatus is suitable for the identification of skin cancers, oral cancers and cervical cancers. The configuration of the apparatus may be specifically arranged depending on the anatomical location of the potential cancer. By way of example, a preferred embodiment of the apparatus for the diagnosis of cervical cancer includes both a non-contacting colposcope (a macroscopic visualization unit) and a contacting fiber optic wand (a microscopic spectral analysis unit).

A colposcope is a device that provides a magnified view of an illuminated area of the cervix, the vagina or the vulva. Cancer and precancerous conditions are usually indicated by the differing appearance of tissues, including for example the presence of abnormal vessels and whitening after application of acetic acid. Cancer is also indicated by different fluorescence than that of normal tissue.

Figure 1:
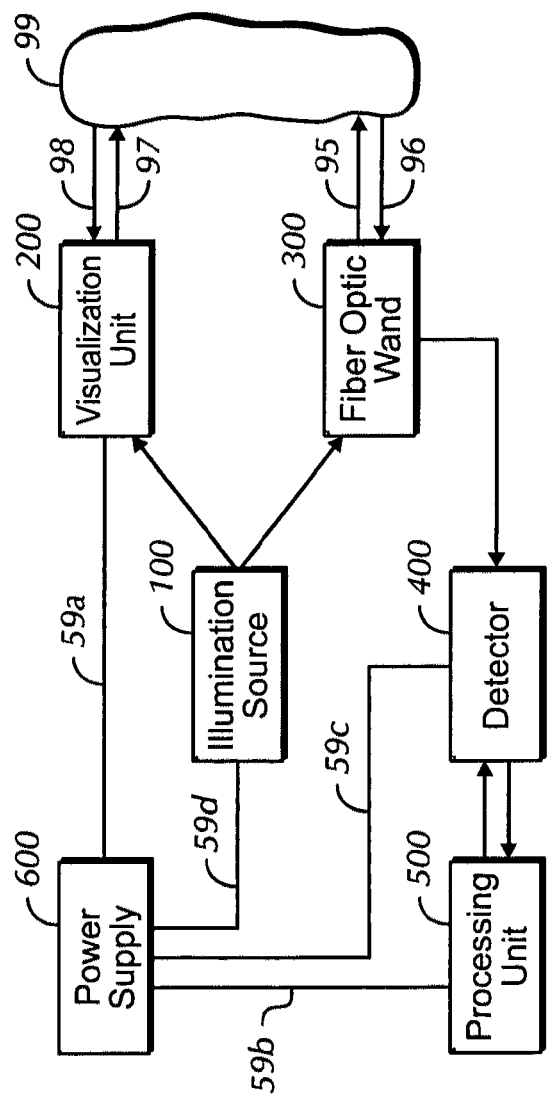
FIG. 1 is a schematic view illustrating the basic components of the medical examination device and their interrelationship.

As illustrated in FIG. 1, the medical examination device has an illumination source 100, a visualization unit 200, an optical probe or fiber optic wand 300, a detector 400, a processing unit 500, and a power supply 600. These basic components may be implemented in a variety of embodiments and can be packaged in a number of configurations without departing from the scope of the invention as set forth in the claims.

I. Basic Components of the Medical Examination Device

The Illumination Source

One of the basic components of the medical examination device is the illumination source 100. The illumination source includes a lamp 105, an emergency shutter 102, optional filters and a light directing device.

One embodiment of the lamp 105 is a Xenon or Mercury arc lamp, while other embodiments include LEDs (light emitting diodes), a Helium Cadmium laser, a halogen lamp, and the like. For example, one embodiment uses a plurality of selectable LEDs. Since LEDs are available that emit a variety of colors or emitted wavelength bands, the use of one or more LEDs can be used to provide the desired wavelength band of the light beam emitted.

Figure 2:
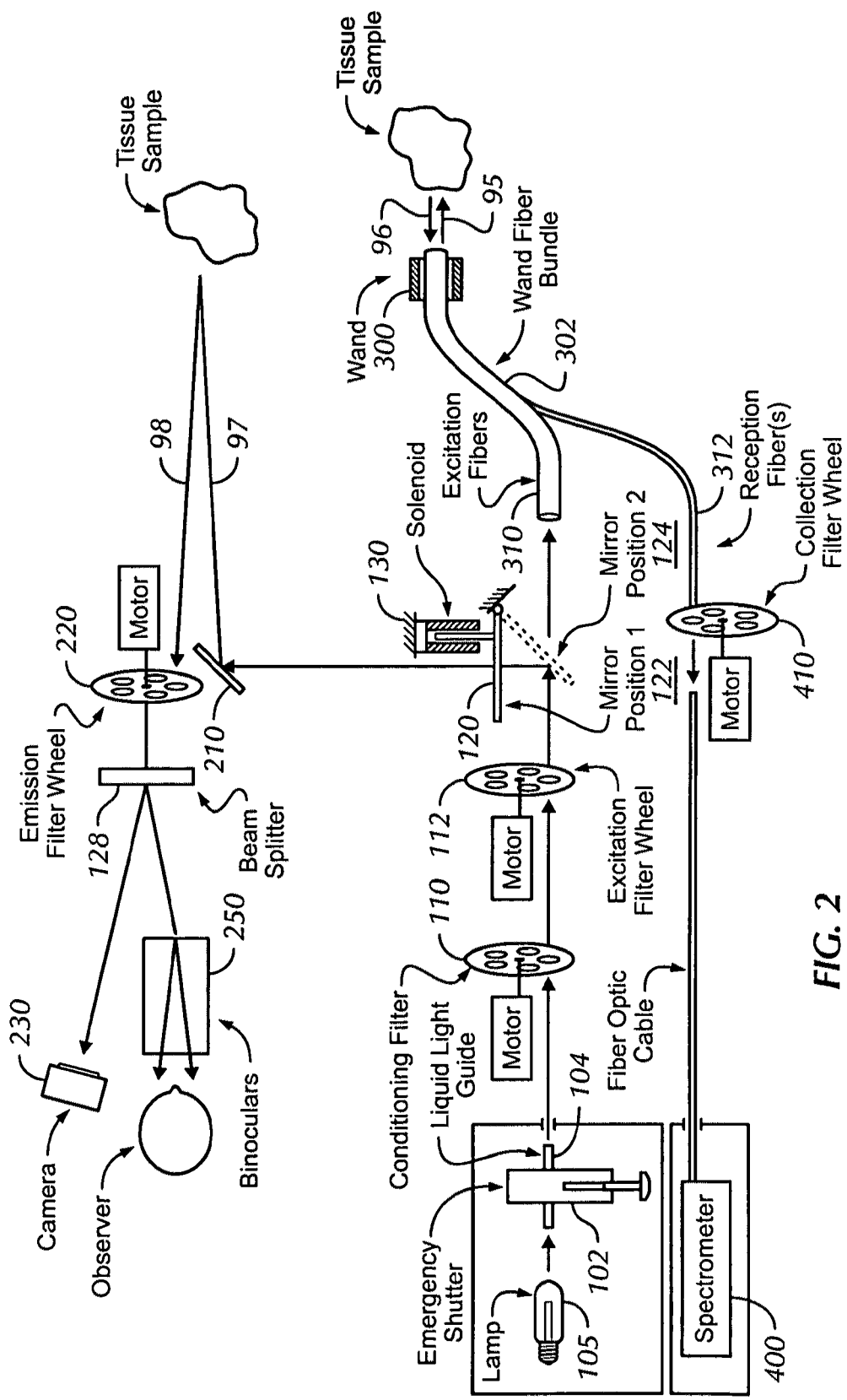
FIG. 2 is a schematic view showing the interrelationship of the components in one embodiment of the device.

The generated light is typically transmitted via a liquid light guide and/or fiber optic cable. The schematic representation of the examination device shown in FIG. 2 illustrates the light generated from lamp 105 transmitted via a liquid light guide 104 through an emergency shutter 102 that can be used to shut off all of the light being transmitted to the tissue in case of an emergency.

The illumination source also includes a light directing device that directs the light to either the visualization unit 200 or the optical probe 300. The medical examination device uses the same illumination source to provide the light beam for the visualization unit 200 or the optical probe 300. The light directing device selectably uses the illumination source for either the visualization unit 200 or the optical probe 300. An advantage of using a single illumination source for both the visualization unit 200 and the optical probe 300 is that the light beam from the light source can be selectably conditioned or filtered at one location before the beam is directed to the visualization unit 200 or the optical probe 300.

A preferred embodiment of the light directing device can reciprocably direct the emitted light beam in either a first direction to the visualization unit 200 or in a second direction to the optical probe 300. For example, one such embodiment of the light directing device is illustrated in FIG. 2. This light directing device includes a mirror 120 that is rotatable between a $1^{st}$ mirror position 122 and a $2^{nd}$ mirror position 124.

The mirror 120 is biased into the $1^{st}$ mirror position 122. The $1^{st}$ mirror position 122 is up and allows the light beam to continue in a forward horizontal direction to enter the excitation fibers 310 of the wand fiber bundle 302. The mirror 120 is moved into the $2^{nd}$ mirror position 124 whenever the solenoid 130 is selectably actuated. The $2^{nd}$ mirror position 124 reflects the light upward to the mirror 210 in the visualization unit 200 which then reflects the light beam 97 to the tissue 99 for assessment by the visualization unit 200. One advantage of using the reciprocable mirror as the light directing device is that a greater percentage of the light intensity is delivered to the tissue than when the light is directed using a beam splitter or dichroic mirror.

An alternative embodiment of the light directing device is shown in FIG. 3. Light from the lamp 105 is transmitted through a fiber optic cable 66 through a lens 64 and/or an excitation filter 65 and into a beam splitter and/or dichroic mirror 122. The beam splitter and/or a dichroic mirror 122 selectably diverts the light into a first forwardly extending horizontal path 97 to the tissue 99 for use in the macroscopic visualization unit 200 or into a second forwardly extending horizontal path 95 for use by the fiber optic wand 300.

Commonly the generated light is conditioned and/or filtered with optical lenses and filters to obtain the desired wavelength band for the light beam used for the medical examination. The light is optionally conditioned or filtered using either one or more selected lenses or filters, or one or more actuated filter wheels containing a number of filters. If the light beam is to be conditioned using a lens and/or a filter, the lens or filter is typically positioned between the lamp 105 emitting the light beam and the light directing device.

The embodiment illustrated in FIG. 2 uses both a motor actuated conditioning filter wheel 110 and a motor actuated excitation filter wheel 112 to prepare the light used to illuminate the tissue 99. These filter wheels may contain any number of filters and/or lenses, such as a polarizer or neutral density filter or fluorescent filter. Alternatively, the light may be conditioned or filtered using one or more individual lenses or filters, such as lens 64 and filter 65 illustrated in FIG. 3.

Fluorescent and/or reflectance spectra are typically used to characterize the pre-cancerous or cancerous condition of the tissue being examined. One or more excitation fluorescence bandwidths may be used, such as 455-465 nm, 410-430 nm, 375-385 nm and/or 340-360 nm, to excite the tissue. Similarly if reflectance is used to examine the tissue, then white light (400-700 nm), or narrower bands such as 455-465 nm, 410-430 nm or 550-590 nm may be used to illuminate the tissue. Parallel and/or cross-polarized light may also be used to enhance different tissue structures.

The Visualization Unit

The visualization unit 200 provides a wide field macroscopic view of the tissue 99. The visualization unit 200 is a non-contacting viewer of the tissue 99 and includes an ocular viewer, like a colposcope, and is referred to herein as the colposcope mode. The visualization unit 200 may optionally include a camera 230. Preferred embodiments will typically include a binocular viewer 250 and an electronic digital camera 230 for displaying, capturing and storing reflectance and fluorescence images of the illuminated tissue 99.

One embodiment of the visualization unit 200 shown in FIG. 2 directs a light beam 97 to the tissue sample 99. The beam of light 98 resulting from the light beam 97 impinging on the tissue sample 99 is optionally filtered or conditioned before being directed to a binocular viewer 250 or to a camera 230 for recording. The embodiment illustrated in FIG. 2 uses a motor actuated filter wheel 220 to filter or condition the beam of light 98 before sending it through a beam splitter 128 that splits the light beam 98 so that the image of the tissue can be seen through both the binocular viewer 250 and the camera 230. Alternatively, a light directing device that directs the light beam 98 to either the binocular viewer 98 or the camera 230 may also be used.

The nature of the light beam 98 will depend on the nature of the impinging light beam 97. For example, if the light beam 97 is white light, then the returning light beam 98 is reflected light. Alternatively, if the light beam 97 is fluorescent light that impinges on the surface of the tissue 99 causing it to fluoresce, then the light beam 98 will be the resultant fluorescence from the tissue 99.

A second embodiment of the visualization unit 200 is illustrated in FIG. 3. The fluorescence or reflected light from the tissue 99 is returned in a beam 98 to the visualization unit 200. This embodiment of the visualization unit 200 passes the light beam 98 through a beam splitter 128, and then optionally conditions or filters the beam 98 using one or more preselected lenses or filters. For example, the beam splitter 128 is shown splitting the light beam 98 through a lens/filter 127 to be visually displayed to a monocular device 240 and through a lens/filter 123 to be photographed by a camera 230.

Alternatively, the same location on the sample may be viewed simultaneously through the ocular viewer .240 and the camera 230 by removing the beam splitter 128 and independently adjusting the optics of the camera 230 and the ocular device 240.

The Fiber Optic Wand

The fiber optic wand or probe 300 provides a microscopic view of a specific site on the tissue 99. The fiber optic wand 300 is a contacting optical probe that delivers a light beam 95 to the tissue 99 via an array of multiple fiber optic excitation strands or fibers 310 and collects the emanated light 96 from the tissue with one or more fiber optic collection strands or fibers 312.

Figure 5:
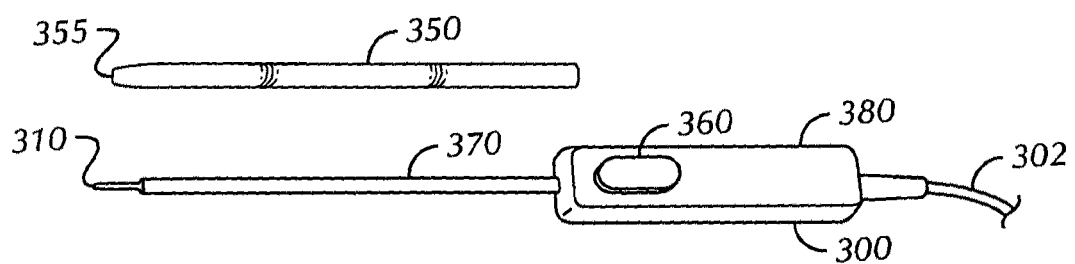
FIG. 5 is an oblique view of the wand from its side on which the on/off switch is mounted, showing the wand with its disposable sheath removed.
Figure 6:
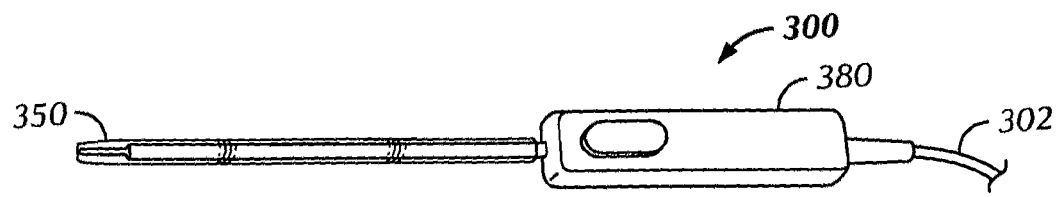
FIG. 6 is a view corresponding to FIG. 6, but with the disposable sheath in position for contact with a patient.

An oblique view of the optical probe 300 is shown in FIGS. 5 and 6. The probe has a shaft 370 with a transverse distal end 310 for placing on a tissue site 99 to be examined. The probe handle 380 is on an opposed proximal end of the probe 300. The embodiment of the wand 300 shown in FIG. 5 has an on/off switch 360 mounted on the handle 380 for selectably activating data acquisition by the probe 300.

A continuous bi-directional fiber optic bundle 302 runs through the handle 380 and the shaft 370 to the transverse distal end 310 of the shaft 370. The fiber optic bundle 302 may be constructed with any number of excitation 310 and collection fibers 312 in any configuration. A cross section of one embodiment of the fiber optic bundle 302 is shown in FIG. 4. In this embodiment, reflected or emitted light is received from the illuminated tissue 99 by a single centrally positioned reception strand (or collection fiber 312) which is surrounded by coaxial multiple outer illumination strands (or excitation fibers 310).

The distal tip 310 of the shaft 370 has a blunted surface or a transverse surface to optimize contact with the tissue. The optical probe 300 has an optional disposable sheath 350 for isolating the shaft 370 from the tissue sample, when the wand 300 is to be used in the clinic. When the sheath is in use, the distal tip 355 of the sheath 350 is blunted to provide good contact between the distal tip 355 and the microscopic tissue area selected for further spectral analysis. The sheath 350 and/or its distal tip 355 is constructed of a material that is non- or minimally light scattering and transparent to the emitted wavelength band of light used for the spectrographic investigation and any reflected or fluorescent light passing back into the wand from the tissue 99. In addition, the material should generate minimal autofluorescence. It should be noted here that when the disposable sheath 350 is positioned on the probe 300 that it is considered a part of the probe and the distal end 355 of the sheath 350 becomes the distal end of the probe 300.

The Detector Unit

The detector unit 400 is used to analyze the collected light emanating from the tissue 99 that is transmitted through the collection or reception strand(s) 312 through fiber optic cable 74. Typically, the detector unit 400 obtains the spectra of the light beam 96 received from the wand 300. The detector unit is primarily a spectrometer 400, although it may include optical components for conditioning and filtering the spectral data transmitted through the collection fiber(s) 312. Such optical components may be a motor actuated collection filter wheel 410 as shown in FIG. 2, or one or more selected individual lens/filter(s) 405 as shown in FIG. 3.

The Processor Unit

The processing unit 500 includes a computer and/or one or more controllers (hereinafter referred to as the computer/controller 580). The processing unit 500 is programmed to configure the operating mechanical and optical components of the medical examination device that are not manually operated. In addition, the computer/controller 580 processes measured and derived data and is able to store and/or transfer such data.

Typically the medical examination device has a computer that coordinates the overall operation of the device and saves patient data, as well as several controllers for activating components such as the solenoid 130 for moving the mirror 120 or activating the motors for positioning the filter wheels to align the desired filter/lens into a beam of light.

Figure 7:
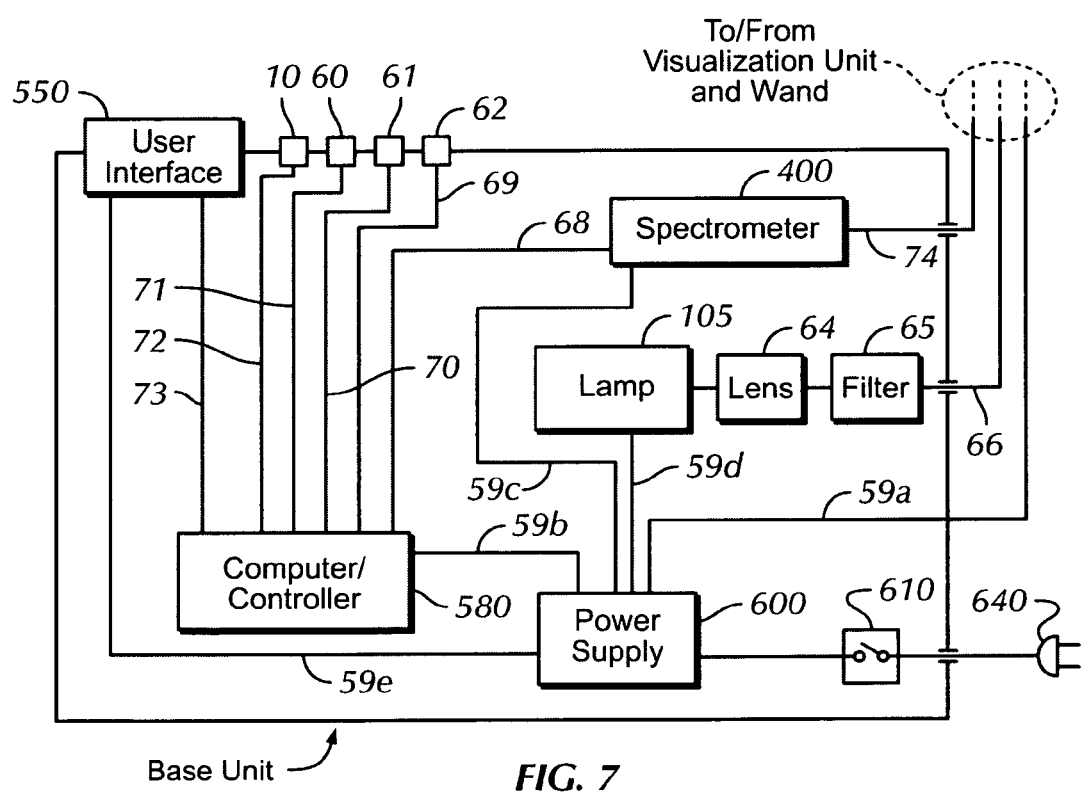
FIG. 7 is a schematic view showing the interrelationship of the computer/control and the power supply with the basic components of the medical examination device.
Figure 8:
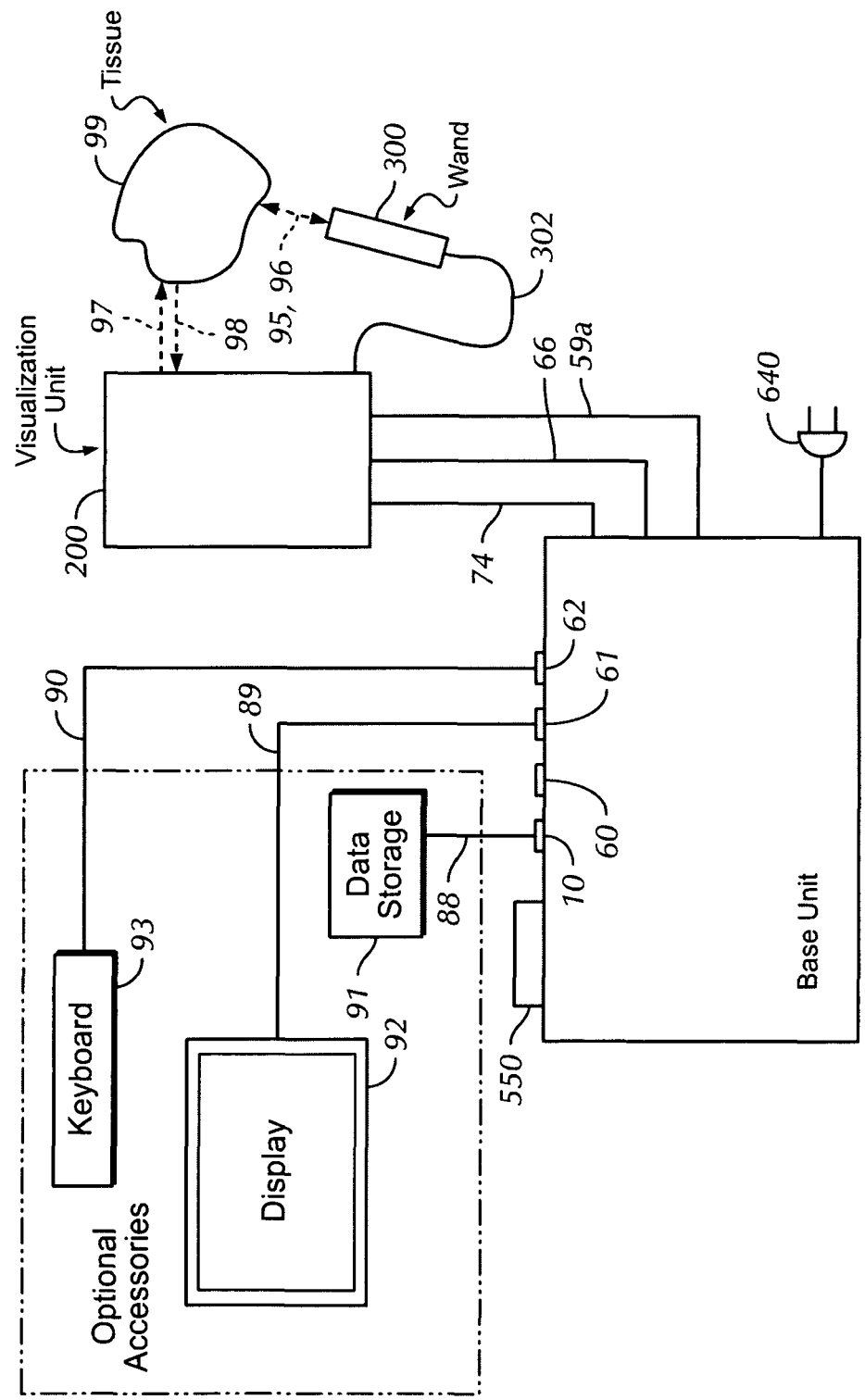
FIG. 8 is a schematic view illustrating the interaction of general components of the device and several optional accessories.

One embodiment of the computer/controller 580 and its interaction with other components of the medical device system is shown in FIG. 7. The embodiment shown in FIG. 7 is provided with multiple bidirectional communication ports 10, 60, 61, and 62 to which data lines 72, 71, 70, and 69 are respectively connected. These communication ports may be used with a variety of optional accessories such as shown in FIG. 8 where port 10 is connected to a data storage device 91 through cable 88, port 61 is connected to an external display 92 through cable 89, and port 62 is connected to an external keyboard 93 through cable 90. An external computer is optionally connected to the computer/controller 580 through one of the ports such as port 60.

The bidirectional data line 73 from the computer/controller 580 to the user interface 550 permits the input of instructions to the computer/controller 580 and the reporting of status to the user through the user interface 550. Furthermore, a data line 68 from the spectrometer 400 to the computer/controller 580 permits data from the spectrometer 400 to be processed by the computer/controller 580 and then stored.

The Power Supply

The power supply 600 for the medical examination device may either be a rechargeable battery pack or supplied through an electrical cord. FIG. 7 shows one embodiment of the power supply 600 and its interactions with other components of the medical examination device.

FIG. 7 illustrates the power supply 600 in series with a main power switch 610 for the device and an electric power cord 640. The power supply 600 regulates output voltages and currents for the various electrical and electronic components of the overall system of the medical examination device. Power from the power supply 600 is fed to the visualization unit 200 via power cable 59a, to the processing unit 500 via power cable 59b, to the detector 400 via the power cable 59c, to the illumination source 100 via the power cable 59d, and to the user interface 550 via the power cable 59e.

The Medical Examination Device

Figure 9:
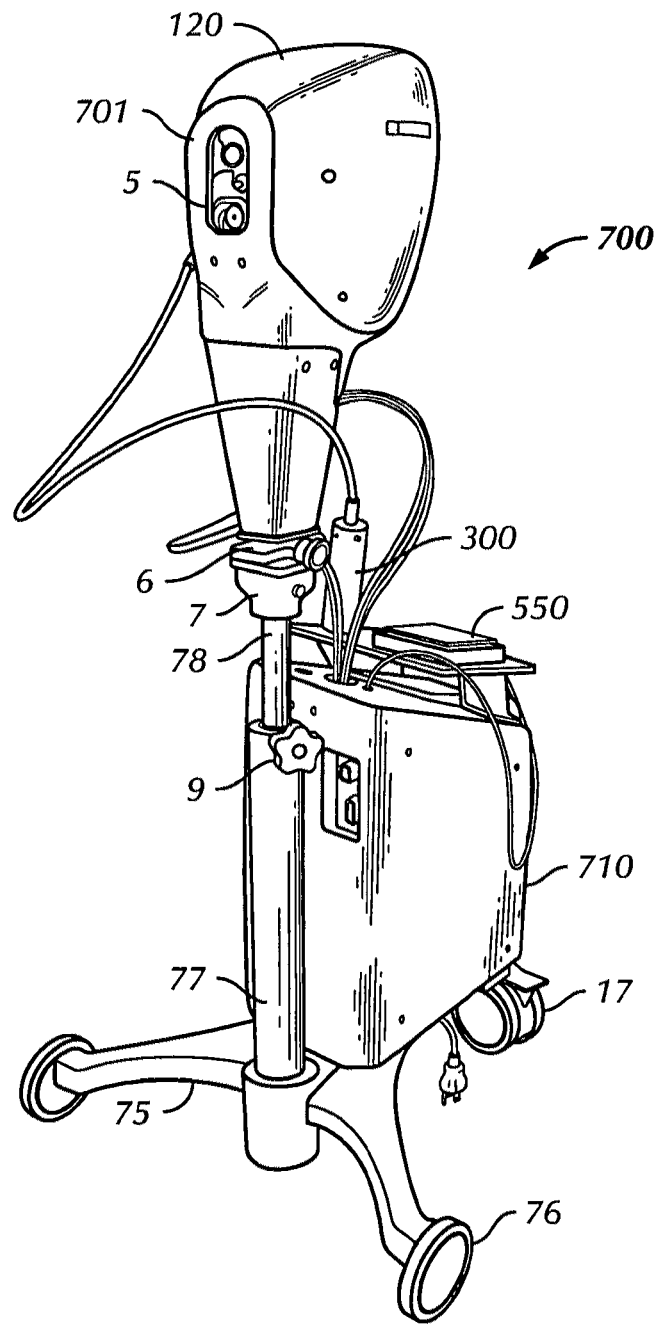
FIG. 9 is an oblique frontal view of the first embodiment of the device.
Figure 10:
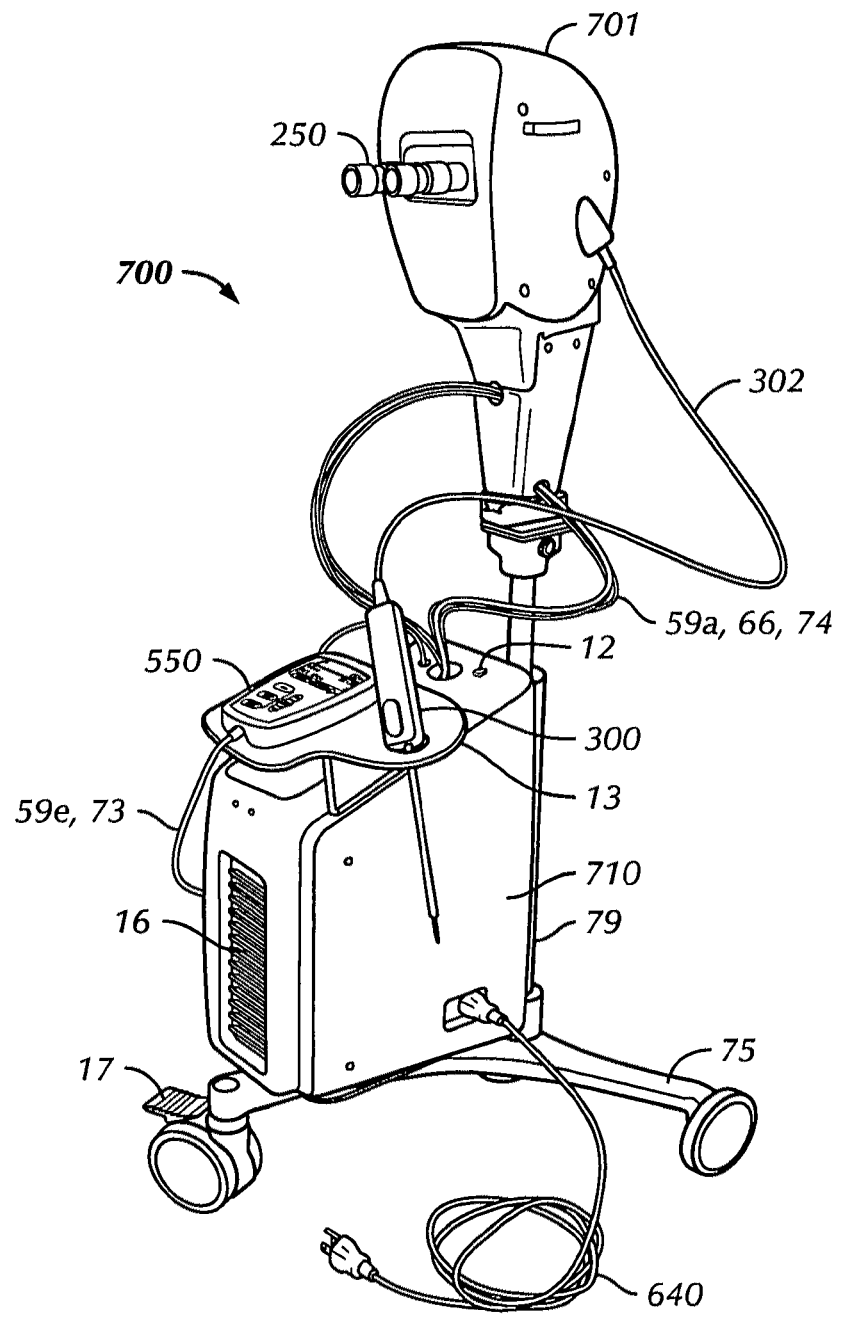
FIG. 10 is an oblique rear view of the device of FIG. 1.

Referring to FIGS. 9 and 10, a first embodiment 700 of the medical examination device is seen in an oblique frontal view and an oblique rear view. The first embodiment of the device 700 includes a viewer unit 701, a base unit 710, and a fiber optic wand 300 as interconnected subassemblies.

In FIG. 9, the medical examination device 700 is seen from the front side, which is the side adjacent the patient and where the light beam 97 is emitted from the visualization unit 200 and the light beam 98 reflected or emitted as fluorescence from the irradiated patient tissue is received. FIG. 10 shows the device 700 from the rear side which is accessed by the human operator when the apparatus is in use.

The lamp 105 may be located in the base unit 710 or the viewer unit 701, depending on the amount of heat generated by the lamp and the heat's dissipation by fans, heat sinks, heat pipes, and the like. Too much heat can adversely affect the life of the lamp 105, as well as the electronics in the spectrometer 400 and in the computer/controller 580.

The visualization unit 200, as see in the schematic representation of FIG. 8, is positioned in the viewer unit 701 and is connected to the power supply 600 located in the base unit 710 by the power cable 59a and fiber-optic cables 66 and 74.

In this first embodiment 700, the lamp 105 is positioned in the visualization unit 200. Fiber optic cable 66 transmits light from the lamp 105 through any selected lenses/filters and to the light directing device. The beam of light is then directed either in a first direction to the tissue 99 as beam 97, or the beam of light is directed to the excitation fibers 310 of the wand fiber optic cable 302 and transmitted to the tissue 99 as beam 95.

Reflectance or fluorescence light from the target specimen 99 in response to beam 97 is returned in a beam 98 to the viewer unit 701, where it is filtered and visually displayed by binoculars 250 and photographed by an electronic camera 230. The camera data is transferred to the computer/controller 580, located in the base unit 710, by an instrument cable (not shown) and images of the tissue 99 from the returning beam 98 may be seen on an external display screen 92.

When the wand 300 of the device 700 is used, the light from the fiber-optic cable 66 is filtered and then focused into the bidirectional fiber optic cable 302. Excitation fibers 310 of the fiber optic cable 302 transfers that light to the wand 300, where it is emitted in a beam 95 upon the target tissue 99.

The light reflected back in a beam 96 from the tissue 99 typically has a different spectral content that the incident light, depending on the character of the cells illuminated in the specimen. This reflected light is transmitted back through the collection fiber(s) 312 of the fiber optic cable 302 to the spectrometer 400 in the base unit 710. The spectrometer 400 is in communication with the computer/controller 580, which is typically positioned in the base unit 710. The computer/controller 580 is generally used to analyze the spectral data obtained from the spectrometer 400 and stored in the data storage device 91.

The base unit 710 has a housing 79 which is mounted on a three leg base 75. The base 75 has three approximately equi-spaced horizontal arms, two of which have nonswiveling fixed casters 76, while the third has a swiveling caster 17 which can be selectably locked.

Extending vertically from the base 75 is a right circular cylindrical tubular mast mount 77. At its upper end, the mast mount 77 is an aperture mounting a mast 78. At the upper end of the mast mount 77 is located a mast height adjustment and lock 9. The mast height adjustment and lock 9 consists of a radially inwardly extending screw with an enlarged handle which is manually operated to loosen or tighten the lock 9 against the mast 78.

The housing 79 mounted on the base unit 710 is typically a blow-molded plastic box having a rectangular horizontal cross-section and a horizontal flat bottom, along with rounded corners. The long horizontal dimension of the housing 79 is oriented with the radially extending horizontal leg of the three-leg base 75 upon which it is mounted. The upper face of the housing 79 slopes slightly downwardly in a radial direction.

On its vertical rear face adjacent the mast mount 77, the housing 79 has an inwardly recessed mounting pocket in which are positioned electrical/electronic connection sockets such as communication ports 10, 60, 61, and 62. On its right side near the bottom is another recessed pocket where the electrical power cord 640 enters the housing 79. A main power switch is also positioned there. Various other penetrations for electrical and fiber-optical cables are provided as needed in the housing 79.

An array of cooling vents 16 is positioned on the rear vertical face of the housing 79 to assist in dissipating any excessive heat buildup within the housing. If necessary, a fan (not shown) can be provided inside the housing 79 to aid maintaining a suitable operating temperature within the housing 79.

An indicator light 12 is shown in FIG. 10 mounted on the upper surface of the housing 79. This indicator light 12 is the startup fault indicator which is connected to the computer/controller 580 and is illuminated when the automated startup and checking routine programmed into the computer/controller 580 experiences a problem.

Planar tray 13 is parallel to and attached to the upper face of the housing 79 and provides additional working space for writing and the like, while a through hole in the right side of the tray provides a stowage position for the loose stabbing mounting of the wand 300. Additionally, the user interface 550 is mounted either to the upper side of housing 79 or to the upper side of tray 13.

The base unit 710 contains the electric power cord 640 in series with the main power switch 610 and a power supply 600. Power from the power supply 600 is fed to the user interface 550 via power cable 59e, to the computer/controller 580 by cable 59b, to the spectrometer 400 by cable 59c, to the xenon arc lamp 105 by cable 59d, and to the viewer unit 701 by power cable 59a.

The computer/controller 580 is programmed to configure the operating mechanical and optical components of the viewer unit 701 and the base unit 710 that are not manually operated. In addition, the computer/controller 580 processes measured and derived spectral data from the spectrometer 400 and then stores, calculates and/or transfers such data.

The computer/controller 580 has communication ports 10, 60, 61, and 62 respectively connected to data lines 72, 71, 70, and 69. A number of optional external electronic accessories are useable with the examination device 700.

The wand 300 has an elongated central small diameter hollow right circular cylindrical stainless steel shaft 370 which is coaxial with the bidirectional fiber optic cable 302 and a coaxial rectangular cross-section handle 380 located at the proximal end of the wand 300. Handle 380 mounts a switch 360 on one side for selectably activating data acquisition by the device.

The distal end of the shaft 370 is reduced in diameter. A continuous bidirectional coaxial light path is provided by fiber optic cable 302 through the handle 380 and the shaft 370 to the transverse distal end 310 of the shaft 370. When in clinical use, a close fitting tubular transparent disposable plastic sheath 350 having a thin transverse distal end 355 is typically interposed over the shaft 370 for sanitary reasons.

The light used by the wand 300 is transmitted to and from the device 700 over the bidirectional fiber optic cable 302. Reflected or emitted light received from the illuminated target tissue 99 is received by a single centrally positioned reception fiber 312 and sent to the spectrometer 400. The coaxial emission fibers 310 that surround the reception fiber 312 send light passed from the viewer unit 701 to the wand 300.

The viewer unit 701 is mounted on top of the extendable mast 78. The viewer unit 701 in turn supports the wand 300. The viewer unit 701 serves a light distribution and capture function for the overall apparatus 700.

The viewer unit 701 has, from its lower end, a tilt and tilt lock adjustment 7 attached to the top end of the extendable mast 78 of the base unit 710, a fine focus and focus lock adjustment 6, and a housing 120 which supports and contains most of the subassemblies and components of the viewer unit 701.

The housing 120 of the viewer unit 701 is hollow and made of blow-molded plastic so that its corners are rounded. The lower portion of housing 120 has a rectangular horizontal cross-section which linearly tapers upwardly where it joins an enlarged upper head portion. The upper head portion extends slightly forward and a relatively larger distance rearward. The upper head is tapered so that it widens and gets taller as it extends rearwardly from the front vertical face. A vertically elongated window 5 is centrally located on the forward vertical face of the upper head, while the rearward vertical face has a central recess where the binocular 250 viewing unit and its rearwardly horizontally extending binocular eyepieces are mounted. The housing 120 is pierced in its lower section to admit the power cable 59a and one or more other electrical data cables (not shown) into the interior of housing 120.

Figure 14:
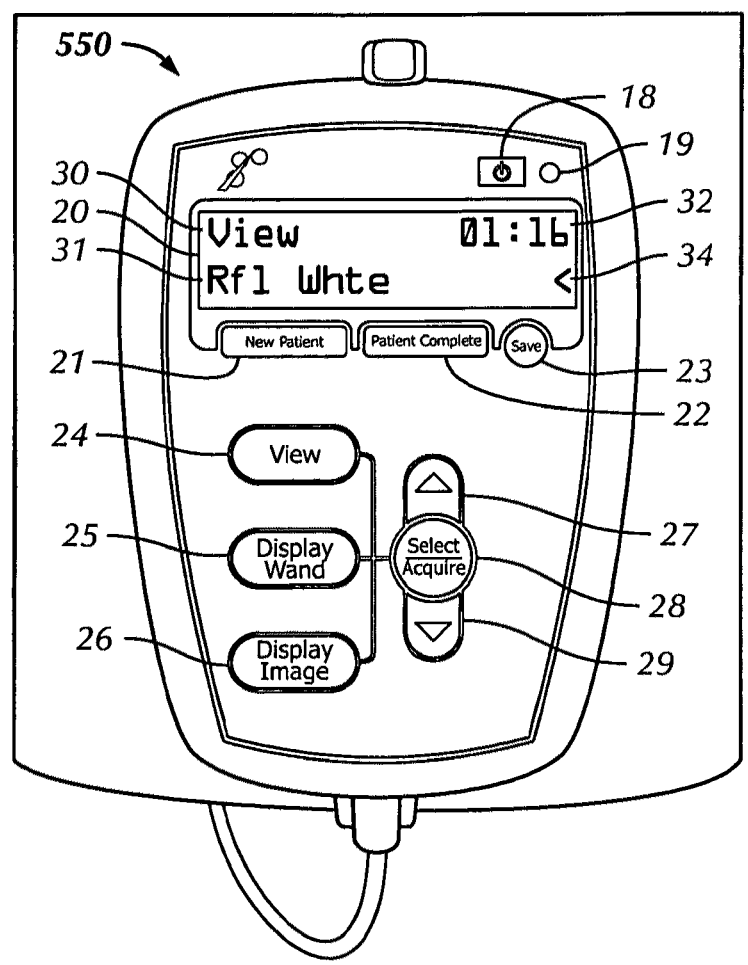
FIG. 14 is a frontal view of the user interface of the device when the visualization unit has been selected for use.
Figure 15:
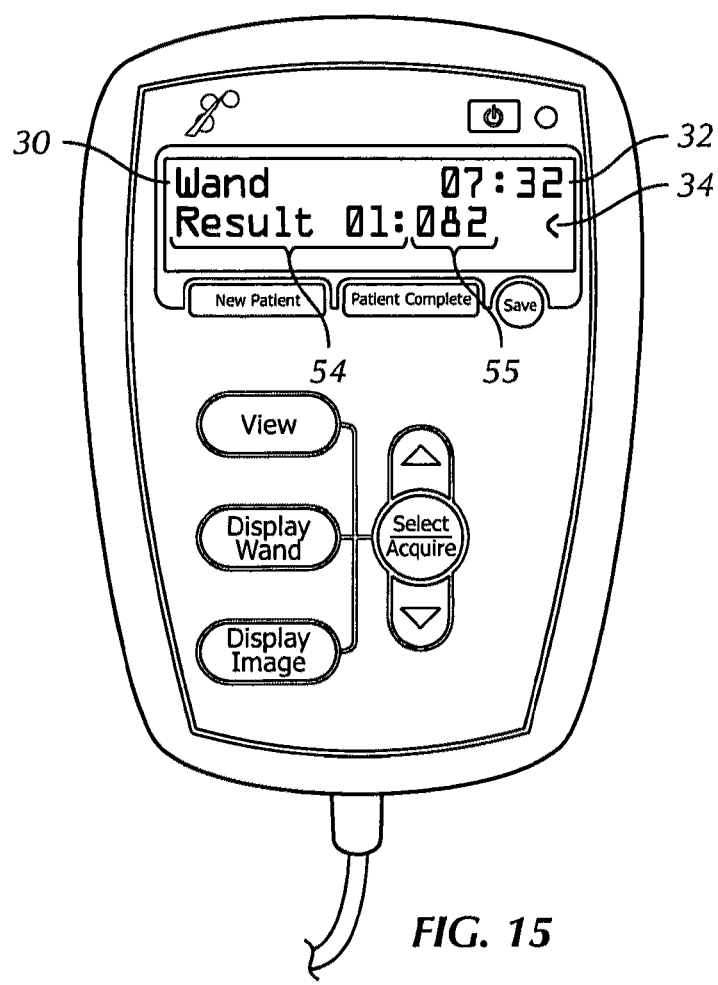
FIG. 15 is a frontal view of the user interface of the device when the optical probe has been selected for use.

The user interface 550 is shown in FIGS. 14 and 15. The user interface 550 is a relatively simple operator interface device with multiple selector switches, status indicator lights, and a liquid crystal display (LCD) for text or graphic signal messages. The user interface can be either permanently mounted onto the upper surface of the housing 79 of the base unit 710 or made separable so that it is connected to the base unit 710 by an intermediate cable containing data line 73 and power line 59e.

Figure 11:
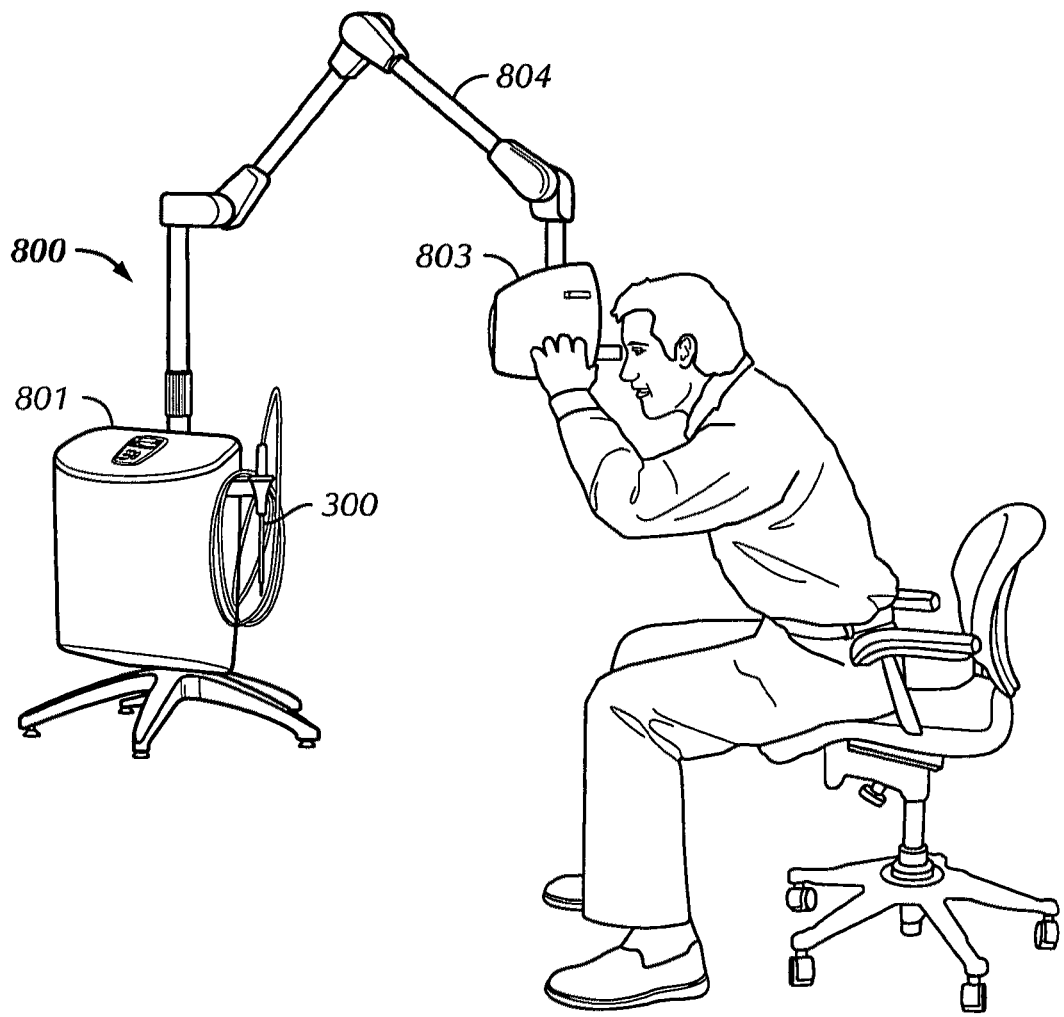
FIG. 11 shows an oblique view of a second embodiment of the medical examination device while in use.

A second embodiment 800 of the medical examination device is seen in use in an oblique side view in FIG. 11, a stowed position side view in FIG. 12, and a stowed position frontal view in FIG. 13.

The second embodiment of the examination device 800 consists of a viewer unit 803, a base unit 801, and a wand 300 as interconnected primary subassemblies. The base unit 801 is functionally similar to base unit 710 of the first embodiment 700, although the base unit is repackaged in order to permit it to stow more compactly and the casters are eliminated. The wand in the device 800 is substantially similar to wand of the first device embodiment 700, except that the wand extends from the base unit 801 rather than the viewer unit 803.

The light directing device illustrated in FIG. 2 is easily configured to direct the light to the wand 300 from the base unit 801. The viewer unit 803 is also functionally similar to viewer unit 701 of the first embodiment. One primary difference is that the viewer unit 803 is mounted on an articulated arm 804 with joints which are either frictionally restrained or restrained by a selectably actuated locking mechanism so that the linkage will remain rigidly in place until the operator elects to reposition it.

Operation of the Medical Examination Device

The medical examination device is connected to a power source. For example, the electrical power cord 640 is plugged into the wall. The power to the medical examination device is turned on at the main power switch 610.

FIGS. 14 and 15 illustrate one embodiment of the user interface 550 that interacts with the medical examination device. The user interface 550 is turned on using a power button 18 located at the upper right side of the user interface device. The power button 18 serves as an off/on switch for the user interface 550, while the power indicator 19 is a status light for showing the power off/on status of the user interface.

Once the power is turned on, the medical examination device undergoes a test of its various components. The base unit electronics are initially tested and if the system passes the base unit test, then the lamp 105 is turned on and the visualization unit is tested and the viewer and camera 230 are calibrated. Then the wand 300 is turned on and calibrated. If all of the components pass the tests and are properly calibrated, then the system either goes into a standby mode, or an operational mode.

An indicator light 12 is shown in FIG. 10 mounted on the upper surface of the housing 79. This indicator light 12 is the startup fault indicator which is connected to the computer/controller 580 and is illuminated when the automated startup and checking routine programmed into the computer/controller 580 experiences a problem. Just below the power button 18 on the user interface 550 is an LCD user interface display 20. If the automated startup and checking routine programmed into the computer/controller 580 experiences a problem, the specific problem will be identified on the user interface display 20 as "Error X" where the X represents a numerical designation of the specific instrument error encountered.

FIG. 14 shows a new patient button switch 21, a patient completion button switch 22, and a save button switch 23, arranged from left to right adjacent the bottom edge of the LCD user interface display 20. Button switches 21, 22, and 23 provide operator instructions to the computer/controller 580.

On the left side of the user interface 550 below the new patient button switch 21, a view button switch 24, a display wand button switch 25, and a display image button switch 26 are sequentially downwardly positioned. These operator selectable switches provide operator instructions to the computer/controller 580. On the right side of the user interface 550 below the patient completion button switch 22, an up button switch 27, a select/acquire button switch 28, and a down button switch 29 are sequentially downwardly positioned.

To begin acquiring patient data, the new patient button switch 21 is pushed to signal the computer/controller 580 to begin. Typically the view mode, or colposcope mode, will be activated first by pressing the view button switch 24. When the visualization unit 200 is on and the display image button 26 is pressed, real time images of a macroscopic region of the illuminated area of the cervix are displayed through the ocular viewer 240, the camera 230, and/or an external monitor display 92. Fluorescent and/or reflectance spectra are typically used for the operator's initial screen of the tissue. The operator of the medical examination device can use these real time reflected images to select a desired area of the tissue for further spectral analysis.

One or more excitation fluorescence bandwidths may be used, such as 455-465 nm, 410-430 nm, 375-385 nm and/or 340-360 nm, to excite the tissue. Similarly if reflectance is used to examine the tissue, then white light (400-700 nm), or narrower bands such as 455-465 nm, 410-430 nm or 550-590 nm may be used to illuminate the tissue. Parallel and/or cross-polarized light may also be used to enhance different tissue structures.

Figures 16, 17:
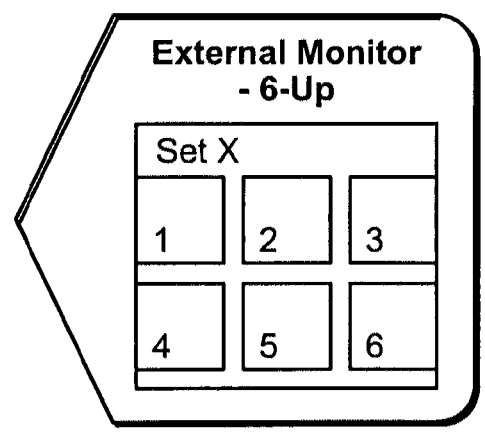
FIG. 16 is a list of names given one example of a set of six different wavelengths of light used to illuminate the cervix.
FIG. 17 is a frontal view of a monitor displaying a set of six images of macroscopic views of the cervix illuminated at different wavelengths of light.

Once the operator has selected a data acquisition area of the tissue 99, the select/acquire button 28 is pressed to signal the computer/controller 580 to begin acquiring an image set for the selected area of illuminated tissue. An image set includes an image captured and displayed on the external monitor for each of the filters used to select particular excitation wavelengths of light, as for example each of the filters in the excitation filter wheel 112. One embodiment of the medical examination device uses six images in a set, three reflectance images (white, blue and violet) and three fluorescent images (ultraviolet, violet and blue). As shown in FIG. 16, each image of the set is associated with a reference number and an abbreviated name for the type of excitation beam used to illuminate the tissue.

Figures 18, 19:
FIG. 18 is a view of the external monitor display when the operator has selected the "View" mode of operation when the visualization unit has been selected for use.
FIG. 19 shows the external monitor display of Wand Results for a set of tissue sites spectrally analyzed using the wand.

Once the images of the tissue have been captured, the display image button 26 is pressed to shut off the light and display the images on the monitor 92. All six of the images may be displayed on the monitor as illustrated in FIG. 17, or a single image may be selected and shown on the monitor as shown in FIG. 18. The up button switch 27, the select/acquire button switch 28, and the down button switch 29 are used to cycle through the images and select the particular image that the operator desires to examine.

The LCD user interface display 20 has several different text or symbolical status displays which are programmed to appear in predetermined locations on the display. Examples of the symbols displayed for the view mode are illustrated in FIG. 14. The upper left corner of the LCD user interface display 20 holds the instrument mode display 30, which in this case indicates the "View" mode associated with use of the visualization unit 200, or the colposcope mode. The lower left corner of the LCD user interface display 20 holds the filter settings display 31, showing in this case that the "Rf 1 White" filter (i.e., white light reflectance) is in use. The upper right corner of the LCD user interface display 20 holds the illumination timer display 32, showing that the tissue was illuminated ("1 minute and 16 seconds"). The lower right corner holds a symbolic indicator 34 which indicates that the illumination is on ("<") or off (">").

FIG. 18 illustrates an external monitor display of a macroscopic view 41 of the illuminated cervix. An electronically displayed set of pertinent sample data is displayed around the periphery of the visual image of the tissue specimen 99 as seen through the binocular 250, the camera 230, and/or on an optional external monitor display 92.

Examples of text or symbolic status displays shown on the monitor showing the real time view of the cervix are also shown in FIG. 18. The top left corner gives the patient identifier 39 ("20070825") and right below the patient identifier is the current filter setting, in this case Filter 5 or a fluorescent, violet light beam for the excitation of the tissue. In the center at the top of the monitor is the illumination timer display and at the top right is a removable, memory capacity indicator 42. At the bottom right hand corner of the monitor is the firmware revision 44 being used to interact with the computer/controller 580 and store the patient images.

The operator may acquire a set of images for a number of areas on the tissue. For example, one embodiment of the medical examination device allows the operator to acquire and store four sets of six images of the tissue for each patient. An experienced operator can select tissue regions that appear abnormal or that are suspect as cancerous or pre-cancerous for further analysis.

Once the operator has examined the cervical images and selected one or more areas for further analysis, the operator may press the view button 24 for a real time view of a cervical area and place the tip 310 of the wand 300 or the distal tip 355 of the disposable sheath 350 in contact with the selected area of the tissue. Generally, the distal tip 310 of the wand and the distal tip 355 of the disposable sheath 350 is blunted or flat to facilitate good contact between the distal tip 310 or 355 with the microscopic area of the tissue selected for spectral analysis. The operator can contact the exact area of the tissue that is desired with the wand 300, because the operator can watch a real-time view of the wand 300 being placed in contact with the tissue while the device is in the view mode.

Once the wand 300 is in place, the display wand button 25 is pressed and the light directing device will direct the beam of light to the optical probe or wand 300. The operator can see the selected contact area on the monitor to further verify the proper placement of the wand 300. The wand 300 is a microscopic probe used to acquire a spectral analysis of one or a few cells of the cervix versus the macroscopic view of the cervix seen by the colposcope mode.

Once the positioning of the wand 300 is verified, the operator can then press the on/off switch 360 mounted on the handle 380 of the wand to selectably activate data acquisition by the probe or wand 300. The probe will deliver the light beam 95 to the tissue 99 via an array of multiple fiber optic excitation fibers 310 and collect the emanated light 96 from the tissue via one or more collection fibers 312.

One or more excitation bandwidths may be used and one or more collection bandwidths may be used for spectral analysis of the tissue. For example, white light (400-700 nm) may be delivered to the tissue and the reflected light collected via the collection fibers 312 and sent to the detector unit 400. Similarly, fluorescent light of one or more wavelengths may be used to excite the tissue and the spectra of the collected light obtained by the detector unit 400 and sent to the computer/controller 580 for spectral analysis.

For example, one embodiment of the wand 300 is programmed to collect and process the four spectral images, one reflectance image and three fluorescent images. The computer/controller 580 uses programmed algorithms to analyze the spectral data collected to assess the likelihood of disease at the site analyzed. The likelihood of disease, pre-cancerous or cancerous tissue changes, is reported as a composite of the four spectra as a probability score between 0 and 100, referred to as the spectroscopic evaluation result or the assessment index.

In FIG. 15, the LCD user interface display 20 shows a typical display when the wand 300 and its associated spectroscopic diagnostic procedures are in use. The instrument mode display 30 shows that the wand 300 has been enabled, while the illumination timer 32 indicates the elapsed time during the wand operation ("07:32"). A wand measurement acquisition number display 54 ("Result") is shown on the left bottom side of the LCD, while a spectroscopic evaluation result 55 ("01:082") is shown as the numerical scale assessment index at the right bottom side of the LCD.

The operator can utilize the wand 300 to acquire a set of spectral images and an assessment index for a number of sites on the tissue. The results of a series of data acquisitions may be shown on the external monitor as illustrated in FIG. 19 and any specific result may be selected using the up button 27, the down button 29 and the select/acquire button 28.

Once the data on a patient has been acquired (i.e., the macroscopic sets of images and the assessment index for a number of tissue sites), the save button is pushed and all of the data is saved and stored under the corresponding patient number. The operator then presses the patient complete button and can begin the assessment of a new patient.

Currently, the likelihood of cervical disease is determined by examining the cervix using a colposcope and performing a biopsy on suspect areas of the cervix. The medical examination device of the present invention provides for an on site evaluation of the cervix for the likelihood of disease with the view mode providing a macroscopic view of the cervix tissue illuminated with various wavelengths of light and a microscopic spectral analysis of various sites in the cervix suspected of disease. Such an on site assessment of cervical tissue negates the need for a patient to reschedule an appointment at a different location and the need to wait for a biopsy report. Thus, the medical examination device makes diagnosis and treatment more readily available and affordable for women.

It should be appreciated by those skilled in the art that the conception and the specific embodiment disclosed might be readily utilized as a basis for modifying or redesigning the medical examination device for carrying out the same purposes as the invention. It should be realized by those skilled in the art that such equivalent constructions do not depart from the spirit and scope of the invention as set forth in the appended claims.

What is claimed is:

1. A medical examination device comprising:
an illumination source, wherein the illumination source includes a lamp and a light directing device for selectably directing a beam of light from the lamp in either a first beam direction or in a second beam direction;
a visualization means positioned a set distance from a region of interest, wherein the visualization means configured for visualizing a first macroscopic image of a first macroscopic tissue site within the region of interest, wherein the visualization means receives the beam of light directed in the first beam direction from the illumination source and radiates the macroscopic tissue site with the received beam of light and visualizes the first macroscopic image from a first emitted light beam emanating from the macroscopic tissue site illuminated with the beam of light directed in the first beam direction a fiber optic probe having a shaft, a handle, and a fiber optic bundle having a plurality of excitation fiber optic strands and a collection fiber optic strand, the excitation fibers and the collection fiber transversing the fiber optic probe from a proximal end of the probe to a transverse distal end of the probe,
- wherein a proxinial end of the excitation fiber optic strands of the probe are optically coupled to the beam of light whenever the beam of light is directed in the second beam direction and wherein the proximal end of the excitation fiber optic strands at the proximal end of the probe collects the coupled beam of light and transmits the beam of light through the excitation fiber optic strands to a distal end of the excitation fiber optical strands at the distal end of the probe configured to illuminate a selected microscopic tissue are within the region of interest when in contact with the transverse distal end of the fiber optic probe,
- wherein the selected microscopic tissue area is within the microscopic tissue site and wherein the visualization means configured to visualize a placement of the distal end of the probe when in contact with the microscopic tissue area when the beam of light is in the first beam direction,
- and wherein a distal end of the collection fiber optic strand collects a second emitted light beam emanating from the microscopic tissue area illuminated with the beam of light transmitted by the excitation fiber optic strands and transmits the second emitted light beam to a proximal end of the collection fiber optic strand at the proximal end of the probe;
- a detector in optical communication with the proximal end of the collection fiber optic strand, wherein the detector detects a plurality of emission wavelengths in the second emitted light beam; and
- a processor for calculating from the detected plurality of emission wavelengths a probability that the microscopic tissue is diseased.

2. The medical examination device of claim 1, wherein the lamp includes a plurality of selectable LEDs.

3. The medical examination device of claim 1, wherein the light directing device includes a mirror that is reciprocable between a first mirror position and a second mirror position.

4. The medical examination device of claim 1, wherein the visualization means includes an ocular device wherein the user of the examination device directly views the illuminated macroscopic tissue site.

5. The medical examination device of claim 1, wherein the visualization means includes a camera for recording the first image of the macroscopic tissue.

6. The medical examination device of claim 1, wherein the collection fiber optic strand is centrally positioned in the fiber optic bundle and is surrounded by multiple coaxial excitation fiber optic strands.

7. The medical examination device of claim 1, further comprising a selectably optically transparent sheath for covering the shaft of the fiber optic probe.

8. The medical examination device of claim 1, wherein the beam of light used to illuminate the selected microscopic tissue area has a wavelength band of 455-465 nm, 410-430 nm, 375-385 nm, or 340-360 nm.

9. The medical examination device, of claim 1, wherein the beam of light used to illuminate the illuminated macroscopic tissue site has a wavelength band of 400-700 nm, 455-465 nm, or 410-430 nm.

10. The medical examination device of claim 8, wherein the beam of light is polarized or unpolarized.

11. A medical examination device comprising:
- an illumination source, wherein the illumination source includes a lamp and a plurality of selectable engageable filters, the lamp generates a beam of light and one of the selectably engageable filters is used to filter the beam of light to a selected wavelength;
- a light directing device for seleetably directing the entire filtered beam of light from the lamp in either a first beam direction or in a second beam direction;
- a visualization means positioned a set distance from a region of interest, wherein the visualizing means configured for visualizing a macroscopic view of an illuminated macroscopic tissue site within the region of interest, wherein the visualization means receives the beam of light directed in the first beam direction, illuminates the macroscopic tissue site with the directed beam of the light directed in the first beam direction, and visualize a first emitted light beam emanating from the macroscopic tissue site illuminated with the directed beam of light directed in the first direction for a direct visualization of the macroscopic view of the illuminated macroscopic tissue site by a user of the examination device;
- a fiber optic probe having a shaft, a handle, and a fiber optic bundle having a plurality of excitation fiber optic strands and a collection fiber optic strand,
    - wherein the fiber optic probe is moveable in relationship to the visualization means and in relationship to the macroscopic tissue site,
    - wherein a microscopic tissue area within the macroscopic tissue is selected and wherein the visualization means configured to visualize a placement of the distal end of the probe when in contact with the microscopic tissue area when the beam of light is in the first beam direction,
    - wherein the excitation strands of the probe are optically coupled to the beam of light whenever the beam of light is directed in the second beam direction and wherein the excitation fiber optic strands transmit the beam of light to illuminate the selected microscopic tissue area limited by a contact surface of the distal end of the fiber optic probe,
    - and wherein the collection fiber optic strand collects a second emitted light beam emanating from the microscopic tissue area illuminated with the beam of light transmitted by the excitation fiber optic strands;
- a detector for detecting a plurality of emission wavelengths from the second emitted light beam;
- a processor in communication with the illumination source, the light directing device, the fiber optic probe, and the detector; and
- a user interface unit in communication with the processor, wherein the user interface unit informs the processor to selectably direct the beam of light in the first beam direction or in the second beam direction and to selectably activate the visualization unit or the fiber optic probe.

12. The medical examination device of claim 11, wherein the visualization means includes a camera for capturing an image of the illuminated macroscopic tissue site for each wavelength of a first set of selected wavelengths.

13. The medical examination device of claim 12, wherein the first set of captured images is displayed on a monitor.

14. The medical examination device of claim 11, wherein the fiber optic probe further comprises a selectably attachable optically transparent sheath for covering the shaft of the fiber optic probe.

15. The medical examination device of claim 14, wherein the distal end of the fiber optical prode and a distal end of the sheath are transverse parallel surfaces when the sheath is attached to the probe.

16. The medical examination device of claim 11, wherein the excitation strands of the fiber optic probe sequentially transmits the beam of light to the selected microscopic tissue area for each wavelength of a second set of selected wavelengths and the collection strand of the fiber optic probe collects the second emitted light beam for each wavelength of the second set of wavelengths.

17. The medical examination device of claim 16, wherein the processor calculates a probability that the microscopic tissue area is diseased from the emission wavelengths detected by the detector in the second emitted light beams collected for the second set of wavelengths.

18. The medical examination device of claim 11, wherein the detector includes a spectrophotometer and a plurality of selectably engageable filters for filtering the second emitted light beam before the second emitted light beam enters the detector.

19. The medical examination device of claim 11, wherein the collection fiber optic strand is centrally positioned and surrounded by multiple coaxial excitation fiber optic strands.

20. A method of detecting cervical cancer comprising the steps of:
generating a beam of light from an illumination source;
directing the entire beam of light in a first beam direction;
illuminating a macroscopic tissue site of a cervix with the beam of light in the first beam direction;
visualizing the illuminated macroscopic tissue site by visualizing an emitted light beam from the illuminated macroscopic tissue site;
selecting a microscopic tissue site within the illuminated macroscopic tissue site for further investigation;
watching a placement of a distal end of a fiber optic probe in contact with the selected microscopic tissue site while the macroscopic tissue site is still illuminated by the beam of light in the first beam direction;
activating a light directing device to direct the entire beam of light in a second beam direction;
generating a set of selected wavelengths from the beam of light by sequentially engaging a set of filters to filter the beam of light from the illumination source;
transmitting the set of wavelengths in the second beam direction to the fiber optic probe having a plurality of excitation optic fibers and a collection optic fiber;
sequentially transmitting the set of wavelengths through the excitation fibers to illuminate the selected microscopic tissue site, wherein a surface area of the microscopic tissue site is less than or equal to a contact surface of the distal end of the fiber optic probe;
sequentially collecting an emitted light beam emanating from the illuminated microscopic tissue site through the collection fiber for each transmitted wavelength;
transmitting each emitted light beam emanating from the illuminated microscopic tissue site to a spectrometer;
conducting a spectral analysis of each emitted light beam emanating from the illuminated microscopic tissue site using the spectrometer to generate a set of spectral data; and calculating as probability that the selected microscopic tissue site is cancerous by comparing the spectral analysis of the selected microscopic tissue site to a spectral analysis of a known non-cancerous tissue site.

21. A method of detecting diseased cervical tissue comprising the steps of:
generating a beam of light from an illumination source having a lamp, a plurality of selectably engageable filters and a light directing device for selectably directing the beam of light in a first direction or a second direction;
directing the entire beam of light in the first beam direction;
illuminating a macroscopic tissue site of a cervix with a first set of selected wavelengths by sequentially filtering the beam of light with a set of the selectably engageable filters to generate the first set of selected wavelengths from the beam of light directed in the first beam direction;
concurrently visualizing and photographing the illuminated macroscopic tissue site by splitting a first set of emitted light beams from the macroscopic tissue site illuminated with the first set of selected wavelengths;
selecting a microscopic tissue site within the illuminated macroscopic tissue site for further investigation;
watching a placement of a transverse distal end of a fiber optic probe in contact with the selected microscopic tissue site while the macroscopic tissue site is still illuminated by the beam of light in the first beam direction;
activating a light directing device to direct the entire beam of light in a second beam direction;
generating a second set of selected wavelengths from the beam of light by sequentially engaging a set of the selectably engageable filters to filter the beam of light from the illumination source, wherein the second set of selected wavelength has at least one wavelength that is contained within the first set of selected wavelengths;
transmitting the second set of wavelengths in the second beam direction to the fiber optic probe having a plurality of excitation optic fibers and a collection optic fiber;
sequentially transmitting the second set of wavelengths through the excitation fibers to illuminate the selected microscopic tissue site, wherein the microscopic tissue site is limited by a contact surface of the distal end of the fiber optic probe;
sequentially collecting a second set of emitted light beams emanating from the illuminated microscopic tissue site through the collection fiber for each transmitted wavelength;
transmitting each emitted light beam of the second set to a spectrometer;
conducting a spectral analysis of each emitted light beam of the second set using the spectrometer to generate a set of spectral data;
recording the set of spectral data in a processor; and
calculating a probability that the selected microscopic tissue site is cancerous using programmed algorithms to analyze the set of spectral data.

* * * * *